United States Patent [19]

Munro

[11] Patent Number: 4,543,413
[45] Date of Patent: Sep. 24, 1985

[54] SULPHONYL DERIVATIVES OF N-PHENYL PYRIDINEAMINES

[75] Inventor: David Munro, Maidstone, England

[73] Assignee: Shell Oil Company, Houston, Tex.

[21] Appl. No.: 602,582

[22] Filed: Apr. 20, 1984

[30] Foreign Application Priority Data

Apr. 22, 1983 [GB] United Kingdom ................. 8311003

[51] Int. Cl.$^4$ ................. C07D 213/61; C07D 213/75; C07D 213/76
[52] U.S. Cl. ..................... 546/305; 346/312; 71/92; 71/94; 544/224; 544/322; 544/327; 544/329; 544/336
[58] Field of Search ................. 546/22, 304, 305, 309, 546/312; 71/92, 94; 544/327, 329, 322, 336, 224

[56] References Cited

U.S. PATENT DOCUMENTS

| | | | |
|---|---|---|---|
| 3,192,222 | 6/1965 | Gross | 546/304 |
| 3,515,744 | 6/1970 | Steinbrunn et al. | 546/309 |
| 3,535,328 | 10/1970 | Zielinski | 260/296 |
| 3,624,096 | 11/1971 | Abramovitch et al. | 546/304 |
| 3,687,959 | 2/1972 | Zielinski | 424/266 |
| 3,926,611 | 12/1975 | Tomlin et al. | 546/312 |
| 3,928,341 | 12/1975 | Delarve et al. | 546/312 |
| 3,960,886 | 6/1976 | Schulenberg | 546/312 |
| 4,082,758 | 4/1978 | McKendry | 546/312 |
| 4,259,330 | 3/1981 | Aller et al. | 546/22 |
| 4,331,670 | 5/1982 | Nishiyama et al. | 546/304 |

FOREIGN PATENT DOCUMENTS

| | | | |
|---|---|---|---|
| 1585082 | 1/1970 | France | 546/312 |
| 475984 | 7/1969 | Switzerland | 546/304 |

Primary Examiner—Henry R. Jiles
Assistant Examiner—Dale A. Bjorkman

[57] ABSTRACT

Aniline compounds having general formula:

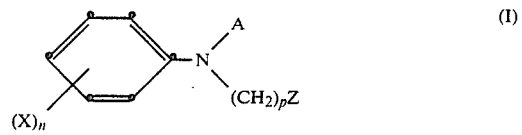

wherein A represents an optionally substituted 6-membered heterocyclic group containing one or two nitrogen atoms; $p=0$ or 1; and Z represents an acyl group of alternatively, when A represents a pyrazinyl group and p is 1, may represent a hydrogen atom; $n=0$, 1 or 2; and X represents a halogen atom or a group R, OH, OR halogen substituted R, COOH, COOR, $NO_2$, CN, or $NH—CO—NH_2$ optionally substituted by R, wherein R is selected from alkyl, alkenyl, alkynyl, cycloalkyl, aryl, aralkyl or alkaryl; or an acid addition salt, N-oxide or metal salt complex thereof, have useful fungicidal, plant growth regulating and herbicidal properties.

4 Claims, No Drawings

SULPHONYL DERIVATIVES OF N-PHENYL PYRIDINEAMINES

The present application relates to aniline compounds, to a process for their preparation, to biologically-active compositions containing them and to a method of combating fungus and/or combating or regulating plant growth.

British patent application No. 8023292 describes a broad class of biologically active heterocyclic amines having the general formula

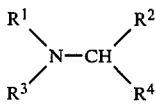

in which one of $R^1$ and $R^2$ represents an optionally-substituted 6-membered heteroaromatic ring containing 1 or 2 nitrogen atoms, and the other of $R^1$ and $R^2$ also represents such a ring or represents an optionally-substituted phenyl group; $R^3$ represents an acyl group derived from a carboxylic acid; and $R^4$ represents a hydrogen atom or an alkyl group having from 1 to four carbon atoms, or an acid addition salt, N-oxide or metal salt complex thereof.

It has now been found that useful fungicidal, herbicidal and plant-growth regulating properties are present in a group of novel tertiary amines in which the nitrogen atom is directly linked to a heterocyclic six-membered nitrogen containing ring, and an optionally substituted phenyl group.

Accordingly the present invention provides aniline compounds having general formula I:

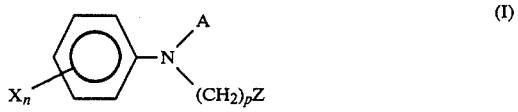

wherein A represents an optionally substituted 6-membered heterocyclic group containing one or two nitrogen atoms; p=0 or 1; and Z represents an acyl group or alternatively, when A represents a pyrazinyl group and p is 1, may represent a hydrogen atom; n=0, 1 or 2; and X represents a halogen atom or a group R, OH, OR, halogen substituted R, COOH, COOR, $NO_2$, CN, or $NH-CO-NH_2$ optionally substituted by R, wherein R is selected from alkyl, alkenyl, alkynyl, cycloalkyl, aryl, aralkyl or alkaryl; or an acid addition salt, N-oxide or metal salt complex thereof.

Unless otherwise stated, any aliphatic moiety present in A, Z or R preferably has up to 6, more preferably up to 4, carbon atoms.

The heterocyclic group represented by A must contain in its ring one or two nitrogen atoms. It need not be unsaturated, although this is preferred, and aromatic unsaturation is preferred in particular. The heterocyclic group may optionally contain one or more substitutents, suitably selected from halogen, in particular chlorine, atoms and groups R, OH, OR, halogen substituted R, COOH, COOR, $NO_2$, CN and $NH-CO-NH_2$ optionally substituted by R, wherein R may be alkyl, alkenyl, alkynyl, cycloalkyl, aryl, aralkyl or alkaryl. In other words, when the 6-membered heteroaromatic group A is substituted, the substituents may be selected from the atoms or groups represented by X. Halogen atoms are the preferred substituent, but most preferably, however, the group represented by A is unsubstituted.

Suitable 6-membered heterocyclic nitrogen-containing groups are the heteroaromatic groups: pyrazinyl; pyridyl; pyrimidinyl; and pyridazinyl. Particularly preferred compounds are those wherein A represents a pyrazinyl or pyridyl group.

The group represented by Z may be an acyl group. In this application "acyl" is used in its widest sense, viz derived from any organic acid by removing one OH-group. Thus "acyl" is not limited to derivatives of a carboxylic acid, but includes also derivatives of sulphonic, carbamic and phosphoric acids. The carboxylic acid may be an arylcarboxylic, alkanoic or dioic acid, and the sulphonic acid may be an alkylsulphonic or an arylsulphonic acid. More preferably, the acyl group Z represents an alkanoyl, carbamoyl, arylsulphonyl or phosphoroyl group, suitably pivaloyl(2,2-dimethylpropanoyl), acetyl, chloroacetyl, methoxyacetyl, propionyl, formyl, butyryl, 3,3-dimethylbutyryl and benzoyl groups, methylcarbamoyl and dimethylcarbamoyl groups; the para-toluenesulphonyl, benzenesulphonyl, para-chlorobenzenesulphonyl and para-aminobenzenesulphonyl groups and the dimethyl- and diethylphosphoroyl groups (also known as di(m)ethoxyphosphoryl groups), including esters and salts thereof. Alkanoyl groups, especially the pivaloyl group, are especially preferred. When A represents a pyrazinyl group and p is 1, then Z may alternatively represent a hydrogen atom.

The group Z may be linked directly to the aniline nitrogen atom, or indirectly, via the alkylene moiety $(CH_2)_p$. Very suitably p=0; in other words, Z is linked directly to the aniline nitrogen atom. Very good results have also been obtained with compounds according to formula I, wherein p=1, A represents a pyrazinyl group and Z represents an alkanoyl group, or, preferably a hydrogen atom.

When the phenyl ring of the compound according to the invention bears a substituent X, it is preferred that one substituent X is in the para position with regard to the aniline nitrogen atom. Preferably X represents a chlorine or fluorine atom, or a methyl, propyl, methoxy, nitro, trifluoromethyl, cyano or dimethylureido group, especially a chlorine or fluorine atom. When n=2, both substituents X need not be the same. The phenyl ring need not be substituted; for instance, the compound according to formula I wherein n=0, A=-pyrazinyl, p=0 and Z=pivaloyl, has good herbicidal properties.

Specific, preferred compounds will be named in the Examples hereinafter.

Depending on the various groups present in the molecule, the compounds of the general formula I may exist in the form of geometric and/or optical isomers. The invention should be understood to include all individual isomers and mixtures thereof.

The invention also provides a process for the preparation of a compound according to the invention in which a N-substituted aniline is coupled with a compound containing the acyl group. Preferably a compound of the general formula

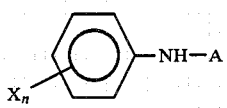

is reacted with a compound of the general formula

Q(CH$_2$)$_p$Z  (III)

wherein X, Z, A, n and p have the meanings defined hereinabove, and Q represents a suitable leaving group. When p=0, this reaction amounts to an acylation of the nitrogen atom.

Suitable leaving groups Q include carboxylates (the compounds of formula III being anhydrides if p=0), and—more suitably—halogen atoms, e.g. bromine or chlorine atoms (the compounds of formula III being acid halides if p=0). Suitably a diluting agent, e.g. a solvent, is present, as well as scavenging agent for the other reaction product, HQ. Preferably the leaving group Q is a halogen atom, and the reaction is preferably carried out in the presence of an acid-binding agent, particularly a base.

When required, these compounds thus prepared are converted into the corresponding acid addition salt, N-oxides and metal salt complexes by methods well known in the art.

Compounds of general formula II are suitably prepared by the reaction of an aniline of formula

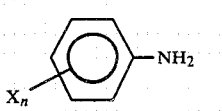

with a chloroheterocycle of formula A—Cl, wherein X, A and n have the meanings defined hereinbefore, preferably in the presence of an acid-binding agent and a diluting agent. The anilines of formula IV are generally known compounds, and often commercially obtainable. The heterocyclic chlorides can also be prepared by methods known per se, or obtained commercially.

The reactions mentioned hereinabove are carried out preferably at temperatures between 0° C. and 180° C., in particular between 20° C. and 150° C., and at atmospheric pressure. Suitable acid-binding agents include all usual organic and inorganic acid-acceptors, e.g. alkali metal carbonates such as Na$_2$CO$_3$ and K$_2$CO$_3$, or tertiary amines, such as triethylamine. Suitable diluting agents include all useful inert organic solvents, e.g. dimethylformamide and toluene. The reactants are generally employed in substantially equimolar quantities, although it may be preferred sometimes to employ one of the reactants in excess to the other; for example an excess of the aniline compound of formula IV may be used.

As mentioned above, the anilines of the invention are of interest as fungicides and plant-growth regulants. Accordingly, the invention includes the use of a compound according to the invention as a fungicide and/or plant growth regulant and a biologically active composition, which comprises a compound according to formula I, together with a carrier.

A carrier in a composition according to the inventon is any material with which the active ingredient is formulated to facilitate application to the locus to be treated, or to facilitate storage, transport or handling. A carrier may be a solid or a liquid, including a material which is normally gaseous but which has been compressed to form a liquid, and any of the carriers normally used in formulating agricultural compositions may be used. Preferably compositions according to the invention contain 0.5 to 95% by weight of active ingredient.

Suitable solid carriers include natural and synthetic clays and silicates, for example natural silicas such as diatomaceous earths; magnesium silicate, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; and chlorinated hydrocarbons, for example carbon tetrachloride, perchlorethylene and trichloroethane. Mixtures of different liquids are often suitable.

Agricultural compositions are often formulated and transported in a concentrated form which is subsequently diluted by the user before application. The presence of small amounts of carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent maybe an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with etheylene oxide and/or propylene oxide; fatty acid esters of glycol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10%w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of active ingredient. Granules are usually prepared to have a size between 10 and 100 BS mesh (1.676–0.152 mm), and may be manufactured by agglomeration or impregnation techniques. Generally, granules will contain ½–75%w active ingredient and 0–10%w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50%w/v active ingredient, 2–20%w/v emulsifiers and 0–20%w/v of other additives such as stabilisers, penetrants and corrosion inhibitors. Suspension concentrates are usually compounded so as to obtain a stable, non-sedimenting flowable product and usually contain 10–75%w active ingredient, 0.5–15%w of dispersing agents, 0.1–10%w of suspending agents such as protective colloids and thixotropic agents, 0–10%w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The compositions of the invention may also contain other ingredients, for example, other compounds possessing herbicidal, plant growth regulating, insecticidal or fungicidal properties.

Also, the present invention provides a method of combating fungus and/or combating or regulating plant growth at a locus, which comprises treating the locus with a compound or a composition according to the invention. The plant growth regulating properties are most evident in compounds according to formula I wherein A represents a pyrazinyl group, and Z represents an alkanoyl or alkoxyalkanoyl group, or A represents a pyridyl group and Z represents an arysulphonyl, suitably benzene sulphonyl, group; p=0; X represents ortho or para halogen or methyl, and n=1 or 2. Amongst the plant growth regulating properties exhibited are a marked growth retardation, accompanied by hyperchromism. In cereals the spikelet number is increased, and in cotton there is a reduction in stem length.

The method of the invention may be used to combat fungus, especially vine downy mildew and peanut leaf spot, and particularly apple powdery mildew and barley powdery milder.

Certain commercial plant-growth regulating compounds have a tendency to produce plants which are more susceptible to fungal attack than the original material. Thus the use as a plant growth regulator of a compound having both plant growth regulating and fungicidal activity would have obvious advantages.

The herbicidal properties of the compounds of the invention are of a rather wide spectrum, so that the compounds can be used as total herbicides, both pre- and post-emergence, but preferably post-emergence. However, rice has a good tolerance for the majority of the present compounds, so that the herbicidal compounds of the invention are especially suited for use in rice fields, particularly for combating undesired growth of broad leaved and grassy weeds.

In the method according to the invention, the compounds of formula I or acid addition salts, N-oxides or metal salt complexes thereof are suitably applied to the locus to be treated at a dosage in the range of from 0.1 to 5 kg/ha, with a range of 0.2 to 1 kg/ha being preferred for plant growth regulating effect, and doses from 1 to 5 kg/ha being preferred for herbicidal action. Most conveniently they are applied in the form of a composition containing the compound(s) together with one or more suitable carriers.

The following Examples illustrate the invention.

EXAMPLE 1

4'-Chloro-N-pyrazinyl-pivalanilide (a) Chloropyrazine (5 g, 44 mmol) and 4-chloroaniline (11.2 g, 88 mmol) were dissolved in 200 ml of xylene, and refluxed with stirring for 4 days. The xylene was removed in vacuo, and the residue was separated by chromatography using silica and ethylacetate. This yielded 6.8 g of unconverted 4-chloroaniline (conversion: 39%), followed by 4 g of a white solid. Recrystallisation of the latter from ethyl acetate/hexane yielded 3.5 g of colourless crystals having a melting point of 165°–167° C. (molar yield 39%). The product was shown to be 4'-chloro-N-pyrazinyl-aniline by NMR spectroscopy and elemental analysis.

(b) Pivaloylchloride (1.4 g) and triethylamine (1.0 g) were added to 80 ml of xylene, and stirred at room temperature under a nitrogen atmosphere for 30 minutes. A quantity of 1 g of the product of step (a) was added, and this mixture was stirred at reflux temperature for 2 hours. A precipitate of triethylamine hydrochloride was removed by filtration. The solvent was removed from the filtrate in vacuo to give a brown oil (1.4 g), which was chromatographed using silica and ethyl acetate to give 1.2 g of a clear oil which solidified. Recrystallisation from hexane gave colourless crystals (1.0 g, 71% molar yield) having a melting point of 96°–97° C. The infrared spectrum confirmed the structure to be that of the title compound.

| Elemental analysis: | % C | % H | % N |
|---|---|---|---|
| calculated for $C_{15}H_{16}ClN_3O$ | 62.15 | 5.55 | 14.5 |
| found | 62.5 | 5.5 | 14.5 |

EXAMPLE 2

4'-Fluoro-N-pyrazinyl-pivalanilide (a) Chloropyrazine (10 g, 88 mmol) and 4-fluoroaniline (20 g, 180 mmol) were dissolved in 40 ml xylene, and refluxed with stirring for 12 hours. The xylene was removed in vacuo and the residue was washed with methylene chloride on a filter to remove the solid precipitate of 4-fluoroaniline hydrochloride. Chromatography using silica and ethylacetate of the washed residue yielded 10.1 g of an off-white solid. Recrystallisation from ethyl acetate gave 9.2 g white crystals of 4'-fluoro-N-pyrazinyl-aniline (55% molar yield), having a melting point of 136°–138° C. The structure was confirmed by IR spectroscopy and elemental analysis.

(b) Pivaloylchloride (13.8 g) and triethylamine (3.2 g) were added to xylene (160 ml) and stirred at room temperature under nitrogen for 30 minutes. The product of step (a) was added (3.0 g), and this mixture was stirred for one hour at reflux temperature. The precipitate of triethylamine hydrochloride was filtered off, and the solvent was removed from the filtrate in vacuo to give 4.2 g of a brown oil. This oil was chromatographed using silica and ethyl acetate to give a clear oil which solidified. Recrystallisation from hexane gave 3.1 g (72% molar yield) colourless crystals having a melting point of 110°–111° C. The infrared and NMR spectra confirmed the structure of the title compound.

| Elemental analysis: | % C | % H | % N |
|---|---|---|---|
| calculated for $C_{15}H_{16}FN_3O$ | 65.95 | 5.85 | 15.4 |
| found | 65.95 | 5.85 | 15.4 |

EXAMPLE 3

4'-Chloro-N-pivaloylmethyl-N-pyrazinyl-aniline (a) 4'-Chloro-N-pyrazinyl-aniline was prepared as described in Example 1 part (a).

(b) The product of step (a) (2.5 g) was dissolved in 100 ml dry tetrahydrofuran, to which 0.4 g of benzene-washed NaH was added, under dry nitrogen. The reaction mixture was refluxed with stirring for 10 minutes, after which a solution of 2.2 g pivaloylmethyl bromide in 20 ml tetrahydrofuran was added dropwise, over a period of 30 minutes. The reaction mixture was then refluxed with stirring for a further hour. The solvent was then removed under reduced pressure, and 80 ml water was added to the dark residue, which mixture was subsequently extracted with methylene chloride (3 times 80 ml). The organic phase was separated off, dried, and the solvent was evaporated in vacuo, to give a dark oil (3.6 g). Chromatography using silica and ethyl acetate gave three products: 1.1 g of the starting material, 0.2 g of a dark brown oil (side-products), and 1.8 g of a brown oil, which solidifed on standing, being the title compound. The solidified brown oil was purified by distillation at 190° C. and a pressure of 0.3 mm Hg. The conversion of the chloropyrazinylaniline was 56%, with a selectivity to the end product of 54% (87% before the destillation).

| Elemental analysis: | % C | % H | % N |
|---|---|---|---|
| calculated for $C_{16}H_{18}ClN_3O$ | 63.25 | 5.95 | 13.85 |
| found | 62.3 | 5.7 | 15.5 |

EXAMPLE 4

4'-Methyl-N-pyrazinyl-dimethylcarbamanilide (N,N-dimethyl-N'-p.tolyl-N'-pyrazinyl-urea)

(a) Chloropyrazine (10 g, 87 mmol) and 4-methylaniline (17.5 g, 164 mmol) were dissolved in 100 ml xylene and heated under reflux for 24 hours. The reaction mixture was allowed to cool and filtered. The filtrate was evaporated in vacuo to remove the solvent giving a brown oil (12.4 g), which was purified by chromatography using silica and a 50/50 mixture of methylene chloride and ethyl acetate, giving 10.1 g of a colourless solid. Recrystallisation from an ethyl acetate/hexane mixture gave 9.4 g colourless crystals of 4'-methyl-N-pyrazinylaniline, having a melting point of 114° C. (molar yield 65%). Infrared spectroscopy and elemental analysis confirmed the structure.

(b) 1.5 g Of the product of step (a) was dissolved in 120 ml toluene, which was saturated with phosgene, and the reaction mixture was refluxed with stirring under a nitrogen atmosphere, while passing phosgene for 30 minutes. The reaction mixture was then refluxed for a further 30 minutes, while passing dry nitrogen, before adding an excess of dimethylamine. Immediately a reaction occurred, as indicated by thin layer chromatography. Preparative chromatography, using silica and ethyl acetate, yielded 1.6 g of a light-brown oil. Distillation thereof yielded 1.2 g of a clear yellow oil (molar yield 64%), having a boiling point of 230° C. at 3 mm Hg. IR and NMR spectra confirmed the structure of the title compound.

| Elemental analysis: | % C | % H | % N |
|---|---|---|---|
| calculated for $C_{14}H_{16}N_4O$: | 65.6 | 6.3 | 21.9 |
| found | 66.2 | 6.7 | 21.8 |

EXAMPLE 5

4'-Isopropyl-N-pyrazinyl-dimethylcarbamanilide (N,N-dimethyl-N'-p.cumenyl-N'-pyrazinyl-urea)

This compound was prepared analogously to Example 4. The molar yield of the last step was 69%. The title compound had a boiling point of 230° C. at 3 mm Hg.

| Elemental analysis: | % C | % H | % N |
|---|---|---|---|
| calculated for $C_{16}H_{20}N_4O$ | 67.6 | 7.05 | 19.7 |
| found | 67.9 | 7.6 | 19.6 |

EXAMPLE 6

4'-Isopropyl-N-pyrazinyl-methylcarbamanilide (N-methyl-N'-p.cumenyl-N'-pyrazinyl-urea)

(a) Chloropyrazine (10 g) and 4-isopropylaniline (18 g) were dissolved in 100 ml xylene, and reacted and purified as in Example 4(a), giving 10.9 g of colourless crystals of 4'-isopropyl-N-pyrazinylaniline, having a melting point of 110° C. (molar yield 65%).

(b) The compound prepared in (a) (1.5 g) was dissolved in 120 ml toluene, to which 3.6 ml methyl isocyanate was added dropwise. The reaction mixture was refluxed under a dry nitrogen atmosphere for six hours. Chromatography of the product gave 1.8 g of a colourless solid (71% molar yield), which was recrystallised from ethyl acetate/hexane to give 1.6 g colourless crystals, having a melting point of 115° C. The IR spectrum confirmed the structure of the title compound.

| Elemental analysis: | % C | % H | % N |
|---|---|---|---|
| calculated for $C_{15}H_{18}N_4O$ | 66.65 | 6.65 | 20.75 |
| found | 66.5 | 6.8 | 20.7 |

EXAMPLES 7-41

By methods analogous to those of Examples 1-6, the following compounds were prepared:

7. 3',4'-dichloro-N-pyrazinyl-pivalanilide, melting point 126° C.
8. 2',4'-dichloro-N-pyrazinyl-pivalanilide, b.p. 170° C. at 0.1 mm Hg.
9. 3'-fluoro-N-pyrazinyl-pivalanilide, m.p. 117°-118° C.
10. 2'-fluoro-N-pyrazinyl-pivalanilide, m.p. 70°-71° C.
11. 4'-nitro-N-pyrazinyl-pivalanilide, m.p. 113°-114° C.
12. 3'-nitro-N-pyrazinyl-pivalanilide, m.p. 101° C.
13. 3'-cyano-N-pyrazinyl-pivalanilide, b.p. 230° C. at 10 mm Hg.
14. 3'-trifluoromethyl-N-pyrazinyl-pivalanilide, m.p. 70° C.
15. N-pyrazinyl-pivalanilide, m.p. 135° C.
16. 4'-methyl-N-pyrazinyl-pivalanilide, m.p. 84° C.
17. 4'-isopropyl-N-pyrazinyl-pivalanilide, m.p. 120° C.
18. 4'-methoxy-N-pyrazinyl-pivalanilide, b.p. 230° C. at 2 mm Hg.
19. 3'-methoxy-N-pyrazinyl-pivalanilide, b.p. 205° C. at 0.3 mm Hg.
20. 4'-fluoro-N-(2-pyridyl)pivalanilide, m.p. 77°-78° C.
21. 4'-fluoro-N-(3,5-dichloro-2-pyridyl)pivalanilide, m.p. 101° C.
22. 4'-fluoro-N-(4-pyridyl)pivalanilide, m.p. 120°-121° C.
23. 4'-fluoro-N-(2-pyrimidinyl)pivalanilide, m.p. 91° C.
24. 4'-fluoro-N-(6-chloro-3-pyridazinyl)pivalanilide, m.p. 139° C.
25. 3',4'-dichloro-N-pyrazinyl-3,3-dimethylbutyranilide, b.p. 230° C. at 10 mm Hg.
26. 4'-fluoro-N-pyrazinyl-3,3-dimethylbutyranilide, m.p. 115° C.
27. 4'-fluoro-N-pyrazinyl-acetanilide, b.p. 185° C. at 3 mm Hg.
28. 2',6'-dimethyl-N-pyrazinyl-chloroacetanilide, m.p. 116° C.
29. 2',6'-dimethyl-N-pyrazinyl-methoxyacetanilide, b.p. 220° C. at 2 mm Hg.
30. 4'-fluoro-N-pyrazinyl-p.chlorobenzanilide, b.p. 200° C. at 0.05 mm Hg.
31. 4'-fluoro-N-pyrazinyl-dimethylcarbamanilide, b.p. 225° C. at 2 mm Hg.
32. 4'-fluoro-N-(2-pyrimidinyl)-dimethylcarbamanilide, m.p. 89° C.
33. diethyl(N-pyrazinyl-4'-fluoroanilido)phosphate, b.p. 180° C. at 0.5 mm Hg.
34. diethyl(N-(2-pyridyl)-4'-fluoroanilido)phosphate, b.p. 160° C. at 0.2 mm Hg.
35. 4'-fluoro-N-pyrazinyl-benzenesulfonanilide, m.p. 89°-90° C.
36. 4'-fluoro-N-pyrazinyl-4-chlorobenzenesulfonanilide, m.p. 105°-106° C.
37. 4'-fluoro-N-(2-pyridyl)-benzenesulfonanilide, m.p. 101°-103° C.
38. 4'-fluoro-N-methyl-N-pyrazinyl-aniline, b.p. 140° C. at 0.3 mm Hg.
39. 4'-fluoro-N-methyl-N-(3-chloropyrazinyl)-aniline, b.p. 170° C. at 0.2 mm Hg.
40. 3'-trifluoromethyl-N-methyl-N-pyrazinyl-aniline, b.p. 125° C. at 0.2 mm Hg.
41. N-methyl-N-pyrazinylaniline, b.p. 150° C. at 1 mm Hg.

EXAMPLE 42

Herbicidal Activity

To evaluate their herbicidal activity, compounds according to the invention were tested using as a representative range of plants: maize, Zea mays (Mz); rice, Oryza sativa (R); barnyard grass, Echinochloa crusgalli (BG); oat, Avena sativa (O); linseed, Linum usitatissisum (L); mustard, Sinapsis alba (M); sugar beet, Beta vulgaris (SB) and soya bean, Glycine max (S).

The tests fall into two categories, pre-emergence and post-emergence. The pre-emergence tests involves spraying a liquid formulation of the compound onto the soil in which the seeds of the plants species mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such formulation.

The solid used in the tests was a prepared horticultural loam.

The formulations used in the tests were prepared by diluting with water, solutions of the test compounds in acetone containing 0.4% by weight of an alkylphenol-/ethylene oxide condensate available under the trade mark TRITON X-155. The acetone solutions were diluted with water and the resulting formulations applied at dosage levels corresponding to 5 kg and/or 1 kg of active material per hectare in a volume equivalent to 600 liters per hectare in the soil spray and foliar spray tests, and at a dosage level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, the thirteen days after drenching the soil and were recorded on a 0-9 scale. A rating 0 indicates growth as untreated control, a rating 9 indicates death. An increase of 1 unit on the linear scale approximates to a 10% increase in the level of effect.

The results of the test are set out in Table I below.

TABLE I

| Compound of Example No. | Soil Drench 10 kg/ha | | | | | | | | Dosage kg/ha | Foliar Spray | | | | | | | | Pre-emergence | | | | | | | |
| --- | --- | --- | --- | --- | --- | --- | --- | --- | --- | --- | --- | --- | --- | --- | --- | --- | --- | --- | --- | --- | --- | --- | --- | --- | --- |
| | Mz | R | BG | O | L | M | SB | S | | Mz | R | BG | O | L | M | SB | S | Mz | R | BG | O | L | M | SB | S |
| 1 | 7 | 6 | 7 | 0 | 2 | 4 | 5 | 5 | 5 | 0 | 0 | 4 | 0 | 0 | 5 | 4 | 5 | 7 | 7 | 8 | 2 | 3 | 2 | 8 | 4 |
| | | | | | | | | | 1 | 0 | 0 | 3 | 0 | 0 | 3 | 3 | 4 | 0 | 0 | 4 | 0 | 0 | 0 | 6 | 0 |
| 2 | 6 | 7 | 8 | 6 | 6 | 6 | 4 | 5 | 5 | 0 | 4 | 6 | 2 | 0 | 2 | 0 | 4 | 7 | 8 | 9 | 6 | 5 | 6 | 6 | 5 |
| | | | | | | | | | 1 | 0 | 0 | 0 | 0 | 0 | 0 | 0 | 4 | 3 | 5 | 8 | 4 | 0 | 4 | 5 | 3 |
| 4 | 0 | 0 | 0 | 2 | 2 | 1 | 2 | 2 | 5 | 0 | 0 | 4 | 0 | 3 | 9 | 5 | 4 | 0 | 0 | 0 | 0 | 0 | 0 | 0 | 0 |
| | | | | | | | | | 1 | 0 | 0 | 3 | 0 | 2 | 6 | 4 | 3 | 0 | 0 | 0 | 0 | 0 | 0 | 0 | 0 |

TABLE I-continued

| Compound of Example No. | Soil Drench 10 kg/ha | | | | | | | | Dosage kg/ha | Foliar Spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 7 | 0 | 4 | 6 | 4 | 0 | 3 | 0 | 0 | 5 | 0 | 0 | 0 | 0 | 4 | 2 | 2 | 0 | 0 | 5 | 2 | 0 | 4 | 7 | 0 | 0 |
| | | | | | | | | | 1 | 0 | 0 | 0 | 0 | 2 | 0 | 0 | 0 | 0 | 0 | 0 | 0 | 4 | 7 | 0 | 0 |
| 8 | 6 | 4 | 6 | 0 | 2 | 5 | 5 | 4 | 5 | 5 | 0 | 6 | 0 | 5 | 6 | 6 | 6 | 5 | 5 | 8 | 3 | 5 | 7 | 7 | 0 |
| | | | | | | | | | 1 | 0 | 0 | 2 | 0 | 4 | 5 | 5 | 4 | 2 | 3 | 7 | 0 | 4 | 7 | 4 | 0 |
| 9 | 2 | 3 | 5 | 2 | 4 | 5 | 7 | 6 | 5 | 0 | 0 | 3 | 2 | 4 | 4 | 5 | 5 | 0 | 4 | 8 | 2 | 0 | 5 | 7 | 4 |
| | | | | | | | | | 1 | 0 | 0 | 0 | 0 | 0 | 3 | 3 | 4 | 0 | 0 | 4 | 0 | 0 | 3 | 4 | 0 |
| 10 | 3 | 4 | 6 | 2 | 4 | 5 | 4 | 3 | 5 | 0 | 0 | 6 | 1 | 5 | 7 | 6 | 5 | 0 | 0 | 8 | 2 | 2 | 5 | 7 | 4 |
| | | | | | | | | | 1 | 0 | 0 | 4 | 0 | 2 | 3 | 5 | 4 | 0 | 0 | 4 | 0 | 0 | 0 | 5 | 0 |
| 11 | 0 | 0 | 3 | 2 | 2 | 4 | 5 | 4 | 5 | 0 | 0 | 2 | 0 | 4 | 2 | 2 | 0 | 0 | 0 | 0 | 0 | 0 | 0 | 0 | 0 |
| | | | | | | | | | 1 | 0 | 0 | 0 | 0 | 2 | 0 | 0 | 0 | 0 | 0 | 0 | 0 | 0 | 0 | 0 | 0 |
| 14 | 0 | 0 | 5 | 4 | 0 | 4 | 4 | 3 | 5 | 0 | 0 | 0 | 0 | 0 | 3 | 3 | 3 | 0 | 4 | 6 | 4 | 2 | 5 | 6 | 0 |
| | | | | | | | | | 1 | 0 | 0 | 0 | 0 | 0 | 0 | 2 | 0 | 0 | 0 | 0 | 0 | 0 | 2 | 4 | 0 |
| 15 | 6 | 6 | 0 | 5 | 4 | 5 | 3 | 4 | 5 | 0 | 0 | 0 | 0 | 0 | 5 | 5 | 6 | 0 | 0 | 8 | 4 | 3 | 5 | 6 | 5 |
| | | | | | | | | | 1 | 0 | 0 | 0 | 0 | 0 | 3 | 3 | 4 | 0 | 0 | 0 | 4 | 0 | 4 | 5 | 2 |
| 16 | 5 | 6 | 3 | 3 | 3 | 4 | 2 | 4 | 5 | 0 | 0 | 5 | 0 | 0 | 4 | 3 | 5 | 0 | 0 | 7 | 0 | 0 | 4 | 5 | 0 |
| | | | | | | | | | 1 | 0 | 0 | 0 | 0 | 0 | 4 | 0 | 4 | 0 | 0 | 0 | 0 | 0 | 0 | 2 | 0 |
| 18 | 4 | 7 | 4 | 2 | 4 | 5 | 3 | 4 | 5 | 0 | 0 | 0 | 0 | 0 | 0 | 0 | 4 | 0 | 0 | 0 | 0 | 0 | 0 | 0 | 0 |
| | | | | | | | | | 1 | 0 | 0 | 0 | 0 | 0 | 0 | 0 | 3 | 0 | 0 | 0 | 0 | 0 | 0 | 0 | 0 |
| 19 | 4 | 5 | 6 | 0 | 4 | 5 | 6 | 6 | 5 | 2 | 0 | 5 | 3 | 2 | 5 | 5 | 5 | 0 | 0 | 0 | 0 | 0 | 4 | 7 | 2 |
| | | | | | | | | | 1 | 0 | 0 | 0 | 0 | 0 | 0 | 2 | 3 | 0 | 0 | 0 | 0 | 0 | 2 | 2 | 0 |
| 25 | 0 | 0 | 0 | 0 | 0 | 0 | 0 | 0 | 5 | 0 | 0 | 0 | 0 | 4 | 4 | 0 | 3 | 0 | 0 | 5 | 2 | 0 | 5 | 5 | 0 |
| | | | | | | | | | 1 | 0 | 0 | 0 | 0 | 3 | 3 | 0 | 2 | 0 | 0 | 0 | 0 | 0 | 4 | 2 | 0 |
| 26 | 7 | 7 | 7 | 6 | 5 | 5 | 3 | 4 | 5 | 4 | 5 | 5 | 0 | 0 | 2 | 0 | 4 | 6 | 8 | 8 | 7 | 5 | 4 | 5 | 5 |
| | | | | | | | | | 1 | 0 | 0 | 0 | 0 | 1 | 0 | 0 | 4 | 3 | 5 | 7 | 4 | 0 | 4 | 4 | 2 |
| 29 | 0 | 5 | 5 | 2 | 3 | 5 | 0 | 4 | 5 | 0 | 0 | 0 | 0 | 0 | 0 | 0 | 0 | 3 | 0 | 4 | 0 | 0 | 0 | 0 | 0 |
| | | | | | | | | | 1 | 0 | 0 | 0 | 0 | 2 | 0 | 3 | 0 | 0 | 0 | 0 | 0 | 0 | 0 | 0 | 0 |
| 30 | 2 | 5 | 3 | 2 | 3 | 3 | 2 | 0 | 5 | 0 | 0 | 3 | 0 | 5 | 4 | 3 | 2 | 0 | 0 | 3 | 0 | 0 | 3 | 7 | 0 |
| | | | | | | | | | 1 | 0 | 0 | 0 | 0 | 2 | 2 | 2 | 0 | 0 | 0 | 0 | 0 | 0 | 0 | 4 | 0 |
| 33 | 0 | 0 | 4 | 0 | 0 | 0 | 4 | 4 | 5 | 0 | 0 | 4 | 2 | 2 | 4 | 3 | 5 | 0 | 0 | 4 | 0 | 0 | 3 | 4 | 1 |
| | | | | | | | | | 1 | 0 | 0 | 0 | 0 | 0 | 0 | 0 | 4 | 0 | 0 | 0 | 0 | 0 | 2 | 0 | 0 |
| 35 | 0 | 0 | 6 | 0 | 0 | 4 | 5 | 5 | 5 | 0 | 0 | 6 | 0 | 4 | 4 | 5 | 5 | 0 | 4 | 8 | 0 | 0 | 4 | 6 | 2 |
| | | | | | | | | | 1 | 0 | 0 | 0 | 0 | 2 | 3 | 3 | 4 | 0 | 0 | 7 | 0 | 0 | 0 | 3 | 0 |
| 36 | 0 | 0 | 0 | 0 | 0 | 0 | 0 | 0 | 5 | 0 | 0 | 0 | 0 | 4 | 0 | 4 | 5 | 5 | 5 | 0 | 0 | 6 | 0 | 0 | 3 | 6 | 3 |
| | | | | | | | | | 1 | 0 | 0 | 0 | 0 | 3 | 2 | 4 | 2 | 0 | 0 | 2 | 0 | 0 | 0 | 2 | 0 |

In addition the above tests, foliar spray tests as described were carried out on a further number of compound. The results of these foliar spray tests are summarised in table II below.

TABLE II

| Compound of Example No. | Dosage kg/ha | Phytotoxicity Rating | | | | | | | |
|---|---|---|---|---|---|---|---|---|---|
| | | Mz | R | BG | O | L | M | SB | S |
| 3 | 5 | 1 | 0 | 5 | 0 | 4 | 5 | 3 | 2 |
| | 1 | 0 | 0 | 2 | 0 | 0 | 3 | 0 | 0 |
| 5 | 5 | 0 | 0 | 7 | 2 | 6 | 8 | 9 | 5 |
| | 1 | 0 | 0 | 4 | 0 | 4 | 4 | 4 | 4 |
| 20 | 5 | 0 | 0 | 7 | 0 | 2 | 6 | 3 | 4 |
| | 1 | 0 | 0 | 2 | 0 | 0 | 0 | 0 | 0 |
| 21 | 5 | 0 | 0 | 4 | 0 | 0 | 3 | 0 | 2 |
| | 1 | 0 | 0 | 3 | 0 | 0 | 2 | 0 | 2 |
| 22 | 5 | 0 | 0 | 6 | 0 | 4 | 6 | 2 | 4 |
| | 1 | 0 | 0 | 0 | 0 | 0 | 0 | 0 | 1 |
| 23 | 5 | 0 | 0 | 5 | 0 | 0 | 0 | 1 | 3 |
| | 1 | 0 | 0 | 0 | 0 | 0 | 0 | 0 | 0 |
| 27 | 5 | 0 | 0 | 0 | 0 | 3 | 0 | 0 | 3 |
| | 1 | 0 | 0 | 0 | 0 | 1 | 0 | 0 | 1 |
| 31 | 5 | 0 | 0 | 6 | 2 | 4 | 8 | 5 | 5 |
| | 1 | 0 | 0 | 0 | 0 | 0 | 0 | 0 | 3 |
| 34 | 5 | 2 | 0 | 6 | 2 | 3 | 3 | 4 | 4 |
| | 1 | 0 | 0 | 3 | 0 | 0 | 1 | 0 | 0 |
| 38 | 5 | 0 | 0 | 0 | 0 | 4 | 7 | 0 | 3 |
| | 1 | 0 | 0 | 0 | 0 | 3 | 3 | 0 | 0 |
| 39 | 5 | 0 | 0 | 3 | 0 | 0 | 3 | 0 | 3 |
| | 1 | 0 | 0 | 0 | 0 | 0 | 0 | 0 | 0 |

EXAMPLE 43

Plant Growth Regulating Activity

Observations were made throughout the tests described in Example 42 of the precise effects on the tests plants of the compounds of the invention. The following effects were observed.

1. Many of the compounds showing herbicidal activity produced a depression in growth—i.e. a reduction in stem height—for some or all of the plant species.
2. Many of the compounds resulted in hyperchromism in the test plants—i.e. the production of very dark green leaves.

Various other symptoms were observed in various tests, including affection of the growing points and inhibition of germination.

EXAMPLE 44

Plant Growth Regulating Activity

A number of compounds were examined in detail for plant growth regulating activities in wheat and cotton. It appeared that the compound of Example 2 produced an increase in the spikelet number of wheat, and a reduction of the number of leaves and of the shoot length of cotton. The results of the latter tests are shown below.

TABLE III

| Number of days after treatment | cotton shoot length (cm) | | | significance level (cm) |
|---|---|---|---|---|
| | control | 0.5 kg/ha | 2.0 kg/ha | |
| 1 | 24.4 | 24.7 | 24.7 | 1.1 |

TABLE III-continued

| Number of days after treatment | cotton shoot length (cm) control | 0.5 kg/ha | 2.0 kg/ha | significance level (cm) |
| --- | --- | --- | --- | --- |
| 14 | 32.0 | 30.3 | 26.3 | 2.5 |

The compound of Example 29 produced a marked increase of the number of spikelets of wheat plants: 78 days after treatment the number was 26.2 (spikelets/plant) for the untreated controls and 27.3 for plants treated at a dose of 0.3 kg/ha/significance level 0.9).

The compounds of Examples 16, 18, 26, 27 and 41 also produced spikelet number increases in wheat, whereas the compounds of Examples 18 and 26 produced shoot length reductions in cotton.

EXAMPLE 45

The fungicidal activity of compounds of the invention was investigated by means of the following tests:

(a) Activity against vine downy mildew (*Plasmopera viticola* Pv.a)

The test is a direct anti-sporulant one using a foliar spray. The lower surfaces of leaves of whole vine plants, are inoculated by spraying with an aqueous suspension containing $10^5$ zoosporangia/ml 4 days prior to treatment with the test compound. The inoculated plants are kept for 24 hours in a high humidity compartment, 48 hours at glasshouse ambient temperature and humidity and then returned for a further 24 hours to high humidity. The plants are then dried and infected leaves detached and sprayed on the lower surfaces at a dosage of 1 kilogram of active material per hectare using a track sprayer. After drying the petioles of the sprayed leaves are dipped in water and the leaves returned to high humidity for a further 72 hours incubation, followed by assessment. Assessment is based on the percentage of the leaf area covered by sporulation compared with that on control leaves.

(b) Activity against vine grey mould (*Botrytis cinerea* Bc)

The test is a direct eradicant one using a foliar spray. The under-surfaces of detached vine leaves are inoculated by pipetting ten large drops of an aqueous suspension containing $5 \times 10^5$ conidia/ml on to them. The inoculated leaves are kept uncovered overnight during which time the fungus has penetrated the leaf and a visible necrotic lesion may be apparent where the drop was made. The infected regions are sprayed directly with a dosage of 1 kg of active material per hectare using a track sprayer. When the spray has dried the leaves are covered with petri dish lids and the disease allowed to develop under the moist conditions. The extent of the necrotic lesion beyond the original drop together with the degree of sporulation is compared with that on control leaves.

(c) Activity against barley powdery mildew (*Erysiphe graminis* Eq.)

The test measures the direct anti-sporulant activity of compounds applied as a foliar spray. For each compound about 40 barley seedlings were grown to the one-leaf stage in a plastic pot of sterile potting compost. Inoculation was effected by dusting the leaves with conidia of *Erysiphe graminis*, spp. *hordie*. 24 hours after inoculation the seedlings were sprayed with a solution of the compound in a mixture of acetone (50%), surfactant (0.04%) and water using a track sprayer. The rate of application was equivalent to 1 kg of active material per hectare. First assessment of disease was made 5 days after treatment, when the overall level of sporulation on the treated pots were compared with that on control pots.

(d) Activity against apply powdery mildew (*Podosphaera leuco tricha*, P.l.)

The test measures the direct anti-sporulant activity of compounds applied as a foliar spray. For each compound, apple seedlings were grown to the three to five leaf stage in a plastic pot of sterile potting compost. Inoculation was effected by spraying the leaves with a suspension in water of conidia of the test species. 48 hours after inoculation the seedlings were sprayed with a solution of the test compound in a mixture of acetone (50%), surfactant (0.04%) and water using a track sprayer. The rate of application was equivalent to 1 kg of active material per hectare. First assessment of disease was made 10 days after treatment, when the overall level of sporulation on the treated pots were compared with those on control pots.

(e) Activity against peanut leaf spot (*Cercospora arachidicola* C.a)

The procedure of (d) above was repeated using peanut seedlings grown to a height of about 15 cm. Assessment of disease was made 14 days after treatment.

The extent of disease control is expressed as a control rating according to the criteria:
0 = less than 50% disease control
1 = 50–80% disease control
2 = greater than 80% disease control
— = not tested /1S and /2S indicate systemic activity, using the same scale of rating, and tested by means of a soil (seed) drench method. The obtained control ratings are set out in Table IV.

TABLE IV

| Compound of Example No. | Pv.a | Bc | Eg | P.l. | C.a |
| --- | --- | --- | --- | --- | --- |
| 1 | 0 | 0 | 2/2S | — | 0 |
| 3 | 0 | 0 | 1 | — | 0 |
| 4 | 1 | 0 | 0 | 0 | 0 |
| 7 | 0 | 0 | 2 | 0 | 0 |
| 11 | 0 | 0 | 2/2S | 2 | — |
| 12 | 0 | 0 | 2 | — | 0 |
| 14 | 0 | 0 | 1/2S | 0 | 0 |
| 16 | 0 | 0 | 1 | 0 | 2 |
| 18 | 1 | 0 | — | 0 | 0 |
| 19 | 0 | 0 | 2 | 2 | — |
| 25 | 0 | 0 | 2 | 2 | 0 |
| 26 | 0 | 0 | — | 2 | 0 |
| 30 | 0 | 1 | 2 | 2 | — |
| 31 | 0 | 0 | 1 | 1 | — |
| 33 | 0 | 0 | 0 | 2 | — |
| 35 | 0 | 0 | 2/1S | 2 | — |
| 36 | 0 | 0 | 2 | 2 | — |
| 38 | 0 | 0 | 0/1S | — | 0 |
| 39 | 0 | 0 | 1 | 0 | 0 |
| 40 | 0 | 0 | 0/1S | 0 | 0 |

I claim:

1. A compound of the formula

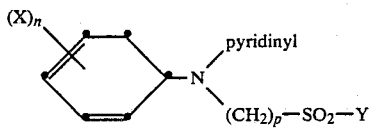

wherein the pyridinyl moiety is bonded from a carbon atom thereof to the indicated nitrogen atom, and is optionally substituted by one or two halogen atoms on carbon atoms of the ring; p is zero or one; n is zero, one or two; X is one of halogen, —OH, —COOH, —NO₂, —CN, —NH—C(O)NH₂, —OR, halogen-substituted R, —C(O)OR, and —NH—C(O)NHR, wherein R is phenyl, alkylphenyl, phenalkyl, alkyl, alkenyl, alkynyl, or cycloalkyl wherein the aliphatic moiety contains up to six carbon atoms; and Y is alkyl of up to six carbon atoms, or phenyl optionally substituted by halogen, amino or alkyl of up to six carbon atoms; or an acid addition salt, N-oxide or metal salt complex thereof.

2. A compound according to claim 1 wherein the pyridinyl moiety is unsubstituted, n is one or two, X is chlorine, fluorine, alkyl of one to three carbon atoms, methoxy, nitro, trifluoromethyl, cyano or dimethylureido, one of X being bonded at the para-position on the ring; and Y is a phenyl moiety as defined in claim 1.

3. A compound according to claim 2 wherein p is zero; X is chlorine or fluorine and Y is phenyl.

4. A compound according to claim 3 wherein n is one; X is fluorine substituted at the 4-position and Y is phenyl.

* * * * *